US009265975B2

(12) United States Patent
Counradi et al.

(10) Patent No.: US 9,265,975 B2
(45) Date of Patent: Feb. 23, 2016

(54) FOAMING PREPARATION WITH A YIELD POINT COMPRISING AN ANIONIC SURFACTANT AND A CROSS-LINKED, ALKALI SWELLABLE ACRYLATE COPOLYMER

(75) Inventors: Katrin Counradi, Hamburg (DE);
Martin Griebenow, Hamburg (DE);
Michaela Kohut, Hamburg (DE);
Stephan Ruppert, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 1840 days.

(21) Appl. No.: 10/573,323

(22) PCT Filed: Sep. 23, 2004

(86) PCT No.: PCT/EP2004/010668
§ 371 (c)(1),
(2), (4) Date: Sep. 28, 2006

(87) PCT Pub. No.: WO2005/030163
PCT Pub. Date: Apr. 7, 2005

(65) Prior Publication Data
US 2007/0161524 A1    Jul. 12, 2007

(30) Foreign Application Priority Data
Sep. 25, 2003  (DE) .................................. 10344527

(51) Int. Cl.
*A61K 8/44*    (2006.01)
*C11D 1/10*    (2006.01)
*C11D 3/37*    (2006.01)
*A61Q 19/10*   (2006.01)
*A61K 8/46*    (2006.01)
*A61K 8/81*    (2006.01)

(52) U.S. Cl.
CPC . *A61Q 19/10* (2013.01); *A61K 8/44* (2013.01); *A61K 8/463* (2013.01); *A61K 8/8147* (2013.01); *A61K 2800/5424* (2013.01); *A61K 2800/596* (2013.01)

(58) Field of Classification Search
CPC ....... A61K 8/44; A61K 8/463; A61K 8/8147; A61K 2800/5424; A61K 2800/596; C11D 1/10; C11D 3/37; A61Q 19/10
USPC ......... 510/127, 135, 143, 155, 158, 426, 434, 510/475, 477, 492; 424/401, 70.16, 70.19, 424/70.22
See application file for complete search history.

(56) References Cited

U.S. PATENT DOCUMENTS

| 5,519,063 | A | 5/1996 | Mondet et al. |
|---|---|---|---|
| 6,056,947 | A | 5/2000 | Kahre et al. |
| 6,280,758 | B1 | 8/2001 | Warren et al. |
| 6,287,583 | B1 | 9/2001 | Warren et al. |
| 6,533,873 | B1 | 3/2003 | Margosiak et al. |
| 6,555,101 | B1 | 4/2003 | Kahre et al. |
| 6,635,702 | B1 | 10/2003 | Schmucker-Castner et al. |
| 2003/0059392 | A1 | 3/2003 | L'Alloret |
| 2003/0147825 | A1 | 8/2003 | Chiarelli et al. |
| 2003/0206955 | A1* | 11/2003 | Sonneville-Aubrun et al. ............................ 424/486 |
| 2004/0023820 | A1* | 2/2004 | Patel ................ 510/130 |
| 2004/0087668 | A1 | 5/2004 | Schmucker-Castner et al. |
| 2004/0234482 | A1* | 11/2004 | Muller et al. .............. 424/70.13 |
| 2005/0032656 | A1 | 2/2005 | Strassner et al. |
| 2005/0048017 | A1 | 3/2005 | Strassner et al. |
| 2005/0158268 | A1 | 7/2005 | Schmucker-Castner et al. |
| 2006/0120986 | A1 | 6/2006 | Albrecht et al. |

FOREIGN PATENT DOCUMENTS

| AU | 760248 | 6/2000 | |
|---|---|---|---|
| DE | 3929973 | 3/1991 | |
| DE | 69204978 | 2/1993 | |
| DE | 4234405 | 4/1994 | |
| DE | 4439542 | 1/1996 | |
| DE | 19814608 | 9/1999 | |
| DE | 19854827 | 6/2000 | |
| DE | 19937813 | * 2/2001 | ............. A61K 7/075 |
| DE | 10107216 | 8/2002 | |
| DE | 10147049 | * 4/2003 | ............... A61K 7/50 |
| DE | 10148393 | 4/2003 | |
| DE | 10221813 | 11/2003 | |
| EP | 1055425 | 11/2000 | |
| EP | 1160005 | 12/2001 | |
| EP | 0738509 | 9/2003 | |
| GB | 2283754 | 5/1995 | |
| WO | 92/13513 | 8/1992 | |
| WO | 95/20641 | 8/1995 | |
| WO | 96/17916 | 6/1996 | |
| WO | 96/17917 | 6/1996 | |
| WO | 97/32559 | 9/1997 | |
| WO | 01/19946 | 3/2001 | |
| WO | 01/76552 | 10/2001 | |
| WO | 03/039498 | 5/2003 | |
| WO | 2004/006870 | 1/2004 | |
| WO | 2004/014333 | 2/2004 | |

OTHER PUBLICATIONS

AkzoNobel. "Product Overview: Structure Plus" (Mar. 8, 2005), pp. 1-2.*
English Language Abstract of DE 101 48 393, Apr. 24, 2003.
English Language Abstract of DE 198 14 608, Sep. 23, 1999.
English Language Abstract of DE 44 39 642, Jan. 11, 1996.
English Language Abstract of DE 102 21 813, Nov. 27, 2003.
English Language Abstract of DE 39 29 973, Mar. 14, 1991.

* cited by examiner (Continued)

*Primary Examiner* — Brian P Mruk
(74) *Attorney, Agent, or Firm* — Abel Law Group, LLP

(57) ABSTRACT

A cosmetic or dermatological cleansing preparation comprising one or more anionic surfactants, one or more gel-forming acrylate thickeners selected from cross-linked, alkali-swellable acrylate copolymers, and, optionally, up to 20% by weight of a mixture of ethoxylated mono-, di- and triglycerides of carboxylic acids having from 8 to 22 carbon atoms.

31 Claims, No Drawings

FOAMING PREPARATION WITH A YIELD POINT COMPRISING AN ANIONIC SURFACTANT AND A CROSS-LINKED, ALKALI SWELLABLE ACRYLATE COPOLYMER

CROSS-REFERENCE TO RELATED APPLICATIONS

The present application is a U.S. National Stage of International Application No. PCT/EP2004/010668, filed Sep. 23, 2004, which claims priority of German Patent Application No. 103 44 527.7, filed Sep. 25, 2003.

BACKGROUND OF THE INVENTION

1. Field of the Invention

The present invention relates to cosmetic cleansing agents. Such agents are known as such. They are essentially surface active substances or substance mixtures that are offered to the consumer in various preparations.

2. Discussion of Background Information

Preparations of this type are, for example, bubble baths and shower baths, solid and liquid soaps or so-called "syndets" (synthetic detergents), shampoos, pastes for hand washing, intimate cleansing agents, special cleansing agents for small children and the like.

Surface-active materials—best known as the alkali salts of higher fatty acids, thus, the standard "soaps"—are amphiphilic materials that can emulsify organic non-polar substances in water.

These materials not only wash dirt off skin and hair, but they also irritate skin and mucous membranes more or less intensely, depending on the selection of surfactant or surfactant mixture.

The most common surfactant for cosmetic preparations is sodium lauryl ether sulfate. Although it has good washing power and good compatibility with skin and mucous membranes, sensitive persons should avoid frequent contact with it.

A large number of quite mild surfactants is indeed obtainable. However, prior art surfactants are either mild but clean poorly or else they clean well, but irritate skin and mucous membranes.

Thus, remedial measures for these drawbacks were to be provided.

In a special embodiment, the present invention relates to cleansing preparations for use as a shower preparation.

Such preparations are also known as such. These essentially are surface active substances or substance mixtures that are offered to the consumer in various preparations. Preparations of such a type are characterized generally by a more or less high water content, but can also be, for example, a concentrate.

In general, preparations, which are designated for the shower, do not or hardly differ from bathtub preparations, except that higher viscosity products that do not run off the hand after removal from the container are preferred for shower preparations. This is of lesser practical significance with bathtub preparations.

In a simple water bath without added surfactant, a swelling of the skin's horny layer occurs first, whereby the degree of this swelling depends, for example, on the duration of the bath and its temperature. Simultaneously, water-soluble materials, for example, water-soluble dirt components, but also materials intrinsic to skin, which are responsible for the water-binding capability of the horny layer, are washed off or out. In addition, skin fats are also dissolved to a certain extent, and washed out by surfactants intrinsic to the skin. This causes, after initial swelling, a subsequent distinct drying of the skin that can again be intensified by detersive additives.

These processes are generally negligible in healthy skin, because the skin's protective mechanism can compensate easily for such slight disturbances in the upper skin layers. However, in cases of non-pathological deviations from the normal status, for example, caused by environmental wear and tear damage or irritation, light damage, aged skin, etc., the protective mechanism of the skin's upper layer malfunctions. It is then possibly no longer able to fulfill its objective on its own and must be regenerated by external measures.

Therefore, the object of the present invention was to remedy this shortcoming of the prior art. Further, an object of the invention was to make available bath preparations, but also shower preparations, which, on the one hand, have a strong care effect without, on the other hand, the cleansing effect being inferior.

The present invention further relates to detersive hair-cosmetic preparations, commonly called shampoos. In particular, the present invention relates to hair-cosmetic active ingredient combinations and preparations for care of the hair and scalp.

Washing the hair with aggressive surfactants can also stress the hair, at least its outward appearance, or degrade altogether the outward appearance of the hairdo. For example, certain water-soluble hair constituents (for example, urea, uric acid, xanthine, keratin, glycogen, citric acid, lactic acid) are leached out by the hair wash.

The prior art lacked shampoo formulations which provide care in a satisfactory manner for damaged hair. Therefore, an object was to remedy these disadvantages of the prior art as well.

Gels are conventional and just recently ever more widely spread forms of cosmetic and dermatological preparations.

Cosmetic gels enjoy extreme popularity with the consumer. As they are generally transparent, often may be colored, but just as often clear colorless, they offer the cosmetics developer additional design possibilities, which partially have a functional character, but partially also serve solely for the improvement of outward appearance. Thus, for example, interesting optical effects can be conferred on the product, which is offered to the viewer generally in transparent packaging, by incorporated color pigments, gas bubbles and the like, but also larger objects.

Then, if it is desired that the incorporated object(s), if recognizable as such with the naked eye, or may be given visible shapes in microscopic dimensions, but in an interesting arrangement—for example in the form of artificially produced color streaks, it is desirable that these objects remain fixed in the gel formulation, and not sink to the bottom or in any way undertake other unpleasant migrations in the formulations.

Liquids can differ with respect to their rheological properties in their flow and deformation behavior. Ideal elastic structures sustain from external forces an elastic deformation, that causes, on removal of the external force, a spontaneous complete recovery from the deformation. Ideal viscous structures are changed irreversibly in their form by external forces. The increasing deformation is called flowing. Most liquids are neither ideally viscous nor ideally elastic, but show viscous as well as elastic properties and are therefore called viscoelastic substances.

In most viscoelastic solutions, dispersed particles or gas bubbles are always falling or rising. They have a finite structure relaxation time. This means that the networks in these systems react to a deformation with a corresponding shear stress. This, however, is relaxed to the zero value in a finite time, so that the entire solution is again in a stable state of rest without stress. This means further that these solutions have a defined zero viscosity, and therefore, reach a constant viscosity value at low shear rates.

In contrast to these systems, there are also such in which dispersed particles or gas bubbles do not settle. It is noticed that these systems flow only above a characteristic value. This value is called yield point. On closer consideration of the rheological properties of these systems, it is striking that the memory module is independent of the oscillation frequency in the entire frequency range and is always substantially greater than the loss module.

Conversely, the value of the complex viscosity does not reach a constant value even at the smallest frequencies, but increases further.

Carbopol gels are cross-linked acrylic acid polymers which bear a high number of carboxyl groups. In dissolved form, these structures bind water. Neutralization of the carboxyl groups leads, due to their electrostatic repulsion, to an extension and therefore, swelling of the polymer chains. In this condition, Carbopol gels attain their typical rheological properties, such as, for example, development of a yield point.

The action of the development of a yield point is based, therefore, on the electrostatic repulsion of the carboxyl groups, Additional electrolytes shield these charges. Consequently the networks collapse, the yield point breaks down. Particles or gas bubbles can no longer be held in suspension.

Surfactants act like electrolytes. Therefore, it was not possible until now to formulate good, foaming cleansing products having a correspondingly high surfactant content and containing, as the base, clear Carbopol gels having a yield point.

The prior art does indeed already disclose corresponding systems with xanthan gum (for example, EP-A 738 509). These have, however, worse cosmetic properties, relative to the feel of the skin, before and after use. Furthermore, only low viscosities can be achieved at identical use concentration. The design of a gel, which, in addition, has suitable flow properties, usually presents no extremely great difficulties to one of skill in the art, unless high surfactant concentrations are to be achieved, as a rule, a basic requirement in cleansing products. The disadvantage of such high surfactant concentrations is that mostly only cloudy or even opaque products are obtained.

WO 01/19946 discloses detersive recipes that contain a conditioner in addition to a gel-former. WO 01/176552 discloses detersive recipes which involve a combination of certain thickeners with acyl glutamates. However, these publications could not point to the present invention.

Another disadvantage of prior art preparations was the poor compatibility of the gel-former used for stabilization with electrolytes in general and ionic surfactants in particular. Such preparations have correspondingly poor product performance, such as, for example, weak foam formation and an unpleasant feel on skin. Furthermore, such products can mostly not be called truly clear.

To be sure, electrolyte-tolerant and surfactant-tolerant gel-formers do exist by all means, but again as a rule, highly impair skin-feeling, because they must be used in comparatively high concentrations. The object of the present invention was, therefore, to find formulations, which permit preparing elastic, surfactant-containing gels having a satisfactory yield point while simultaneously avoiding a dull skin-feeling during and after use.

In addition, for the development of a yield point that suffices to stably suspend different particles, gas bubbles or effect materials, quantities of gel-formers are used, which also lead to a considerable increase in product viscosity in addition to the development of a yield point or an increase in elastic modulus. This impairs removal by the consumer, draining residues, distributability of the product, and foaming during use.

Therefore, the object of the present invention was to find ways that permit the preparation of elastic, surfactant-containing gels having a satisfactory yield point with simultaneously comparatively low viscosity.

Thus, remedies for these disadvantages of the prior art were to be provided as well.

SUMMARY OF THE INVENTION

The present invention provides a cosmetic and/or dermatological cleansing preparation. The preparation comprises (a) one or more anionic surfactants, (b) optionally, one or more further surfactants, (c) one or more gel-forming acrylate thickeners selected from cross-linked, alkali-swellable acrylate copolymers, (d) optionally, up to 20% by weight, based on the total weight of the preparation, of a mixture of ethoxylated mono-, di-, and triglycerides of carboxylic acids having from 8 to 22 carbon atoms, and (e) optionally, one or more suspended objects selected from solid particles, gas bubbles and/or liquid droplets.

In one aspect, the preparation of the present invention may further comprise water.

In another aspect, component (a) of the preparation may comprises one or more disodium acyl glutamates. For example, component (a) may comprise one or more of disodium lauroyl glutamate, disodium cocoyl glutamate, disodium myristoyl glutamate, disodium stearoyl glutamate, and disodium tallowyl glutamate.

In yet another aspect, component (a) may be present in an amount of from 0.1% to 5% by weight, e.g., from 0.5% to 4% by weight or from 1% to 3% by weight, relative to the total weight of the preparation.

In a still further aspect, component (c) of the preparation of the present invention may comprise a copolymer of (i) one or more acrylate monomers, (ii) one or more $\alpha,\beta$-ethylenically unsaturated monomers and (iii) one or more polyunsaturated monomers suitable for partial cross-linking. For example, component (i) may comprise one or more of acrylic acid, methacrylic acid, itaconic acid, fumaric acid, crotonic acid, aconitic acid, and maleic acid and/or component (ii) may comprise one or more unsaturated monomers of general formula $CH_2=CXY$ with $X=H$, $C_{1-30}$ alkyl, $-CH_2-(C=O)$ $O(CH_2-CH_2-O)_x-R^3$, $-CH_2-C(=O)NH(CH_2-CH_2-O)_x-R^3$, $-CH_2-CH_2-(CH_2-CH_2-O)_x-R^3$ with $x=1-100$ and $R^3=C_{1-30}$ alkyl or Cl and $Y=-COOR$, $-C_6H_4R$, $-CN$, $-CONH_2$, $-Cl$, $-NC_4H_6O$, $-NH(CH_2)_3COOH$, $-NHCOCH_3$, $-CONHC(CH_3)_3$, $CON(CH_3)_2$, $-CH=CH_2$, $C_{1-18}$ alkyl, hydroxy-$C_{1-18}$ alkyl, $-C(=O)O(CH_2-CH_2-O)_x-R^3$, $-C(=O)NH(CH_2-CH_2-O)_x-R^3$, $-CH_2=(CH_2-CH_2-O)_x-R^3$ with $x=1-100$ and $R^3=C_{1-30}$ alkyl or $CH_2=CH(OCOR^2)$ with $R^2=C_{1-18}$ alkyl or $CH_2=CH_2$ or $CH_2=CHCH_3$.

In another aspect, component (c) may be present in an amount of from 0.1% to 8.0% by weight, e.g., from 0.3% to 6% by weight, or from 0.5% to 4% by weight, relative to the total weight of the preparation.

In another aspect of the preparation, component (d) may comprise one or more ethoxylated glycerin fatty acids, for example, one or more ethoxylated glycerin fatty acids selected from PEG-10 olive oil glycerides, PEG-11 avocado oil glycerides, PEG-11 cocoa butter glycerides, PEG-13 sunflower oil glycerides, PEG-15 glyceryl isostearate, PEG-9 coconut fatty acid glycerides, PEG-54 hydrogenated castor oil, PEG-7 hydrogenated castor oil, PEG-60 hydrogenated castor oil, jojoba oil ethoxylate, PEG-26 jojoba fatty acids, PEG-26 jojoba alcohol, glycereth-5 cocoate, PEG-9 coconut fatty acid glycerides, PEG-7 glyceryl cocoate, PEG-45 palm kernel oil glycerides, PEG-35 castor oil, olive oil PEG-7 ester, PEG-6 caprylic acid/capric acid triglycerides, PEG-10 olive oil glycerides, PEG-13 sunflower oil glycerides, PEG-7 hydrogenated castor oil, hydrogenated palm kernel oil glyceride-PEG-6 ester, PEG-20 corn oil glycerides, PEG-18 glyceryl oleate/cocoate, PEG-40 hydrogenated castor oil, PEG-40 castor oil, PEG-60 hydrogenated castor oil, PEG-60 corn oil glycerides, PEG-54 hydrogenated castor oil, PEG-45 palm kernel oil glycerides, PEG-35 castor oil, PEG-80 glyceryl cocoate, PEG-60 almond oil glycerides, PEG-60 evening primrose glycerides, PEG-200 hydrogenated glyceryl palmate, and PEG-90 glyceryl isostearate.

In another aspect, the preparation may comprises from 0.1% to 20% by weight, e.g. from 1% to 4% by weight, of one or more ethyoxylated mono-, di-, and triglycerides of fatty acids having an average degree of ethoxylation of from 3 to 20 ethylene oxide units, e.g., from 5 to 10 ethylene oxide units.

In yet another aspect, the preparation of the present invention may comprise a gel. Further, gaseous, solid, and/or liquid objects may be embedded in the gel.

In a still further aspect, the preparation may comprise not more than 0.5% by weight of cationic polymers, for example, substantially no cationic polymers.

The present invention also provides a cosmetic and/or dermatological cleansing preparation which comprises (a) from 0.1% to 5% by weight, based on the total weight of the preparation, of one or more disodium acyl glutamates, (b) optionally, one or more further surfactants, (c) from 0.1% to 8.0% by weight, based on the total weight of the preparation, of one or more gel-forming acrylate thickeners selected from cross-linked, alkali-swellable acrylate copolymers, (d) optionally, up to 20% by weight, based on the total weight of the preparation, of a mixture of ethoxylated mono-, di-, and triglycerides of carboxylic acids having from 8 to 22 carbon atoms, (e) optionally, one or more suspended objects selected from solid particles, gas bubbles and/or liquid droplets, and (f) from 5% to 95% by weight, based on the total weight of the preparation, of water.

In one aspect of the preparation, component (a) may comprise one or more of disodium lauroyl glutamate, disodium cocoyl glutamate, disodium myristoyl glutamate, disodium stearoyl glutamate, and disodium tallowyl glutamate.

In another aspect, component (a) may be present in an amount of from 0.5% to 4% by weight, relative to the total weight of the preparation.

In another aspect, component (c) may comprise a copolymer of (i) one or more acrylate monomers, (ii) one or more α,β-ethylenically unsaturated monomers and (iii) one or more polyunsaturated monomers suitable for partial cross-linking.

In yet another aspect, component (c) may be present in an amount of from 0.3% to 6% by weight, relative to the total weight of the preparation.

In a still further aspect, component (a) may be present in an amount of from 1% to 3% by weight and component (c) may be present in an amount of from 0.5% to 4% by weight, each relative to the total weight of the preparation.

In another aspect, the preparation may comprise from 1% to 4% by weight of one or more ethyoxylated mono-, di-, and triglycerides of fatty acids having an average degree of ethoxylation of from 5 to 10 ethylene oxide units.

In another aspect, the preparation may comprise a gel. For example, gaseous, solid and/or liquid objects may be embedded in the gel.

In yet another aspect, the preparation may be substantially free of cationic polymers.

DETAILED DESCRIPTION OF THE INVENTION

It has surprisingly been shown, and herein lies the solution for these objectives, that cosmetic and dermatological detersive preparations containing
(a) an effective amount of one or more anionic surfactants, particularly disodium acyl glutamate,
(b) if desired, further anionic, nonionic, amphoteric, and/or zwitterionic surfactants,
(c) an effective amount of one or more gel-forming acrylate thickeners, selected from the group of cross-linked alkali-swellable acrylate copolymers,
(d) if desired, up to 20% by weight of a mixture of ethoxylated mono-, di-, and triglycerides of saturated and/or unsaturated, linear and/or branched carboxylic acids having from 8 to 12 carbon atoms,
(e) if desired, one or more suspended particles selected from the following group:
   (i) solid particles
   (ii) gas bubbles
   (iii) liquid droplets,
(f) if desired, further conventional auxiliaries and/or additives, particularly water; remedy the disadvantages of the prior art.

One of skill in the art could not anticipate that the preparations according to the present invention would form clear gels having outstanding rheological properties, which, furthermore, would also be suitable in an excellent manner as detersive substances. Cosmetic and/or dermatological cleansing preparations in the sense of the present invention are based on simple and economical recipes. They have simultaneously good foam development and high cleansing power. The preparations act in a regenerating manner relative to the general skin condition, diminish the skin's dryness feeling, and make the skin supple.

Furthermore, according to the teachings of the present inventions, clear preparations having high transmission values are obtainable, for example, such that have a transmission value >70%.

Preferred anionic surfactants are disodium acyl glutamates.

Disodium acyl glutamates are characterized by the following structures:

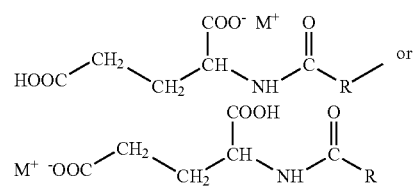

Of the disodium acyl glutamates used according to the invention, disodium cocoyl glutamate, disodium lauroyl glutamate, disodium myristoyl glutamate, disodium stearyl glutamate, and disodium tallowyl glutamate haven proven to be especially advantageous.

The preferred disodium acyl glutamate is disodium cocoyl glutamate.

The total quantity of one or more disodium acyl glutamates used according to the invention in the finished cosmetic or dermatological preparations is advantageously selected from the range of 0.1-5% by weight, preferably 0.5-4% by weight, particularly preferred 1-3% by weight, relative to the total weight of the preparations.

Further advantageous are compounds which bear the INCI designation "acrylates/C12-24 pareth-25 acrylate copolymer" (obtainable under the trademark Synthalen® W2000 from 3V, Inc.), the INCI-designation "acrylates/steareth-20 methacrylate copolymer" (obtainable under the trademark Aculyn® from International Speciality Products Corp.), the INCI designation "acrylates/steareth-20 itaconate copolymer" (obtainable under the trademark Structure 2001® from National Starch), the INCI designation "acrylates/aminoacrylates/C10-30 alkyl PEG-20 itaconate copolymer" (obtainable under the trademark Structure Plus® from National Starch), and similar polymers.

An advantageous acrylate thickener to be used according to the invention is a product sold by the company Noveon under the designation Aqua SF-1. It is a lightly cross-linked, alkali-swellable acrylate copolymer containing three structural components, specifically one or more carboxylic acid monomers having from 3 to 10 carbon atoms, one or more vinyl monomers, and one or more polyunsaturated monomers as the third component.

The total quantity of one or more acrylate thickeners used according to the invention in the finished cosmetic or dermatological preparations is advantageously selected from the range of 0.1-8.0% by weight, preferably 0.3-6% by weight, particularly preferred 0.5-4% by weight, relative to the total weight of the preparations.

Advantageous according to the invention are the ethoxylated mono-, di-, and triglycerides selected from the group of ethoxylated glycerin fatty acid esters, particularly preferred: PEG-10 olive oil glycerides, PEG-11 avocado oil glycerides, PEG-11 cocoa butter glycerides, PEG-13 sunflower oil glycerides, PEG-15 glyceryl isostearate, PEG-9 coconut fatty acid glycerides, PEG-54 hydrogenated castor oil, PEG-7 hydrogenated castor oil, PEG-60 hydrogenated castor oil, jojoba ethoxylate (PEG-26 jojoba fatty acids, PEG-26 jojoba alcohol), glycereth-5 cocoate, PEG-9 coconut fatty acid glycerides, PEG-7 glyceryl cocoate, PEG-45 palm kernel oil glycerides, PEG-35 castor oil, olive oil PEG-7 ester, PEG-6 caprylic acid/capric acid triglycerides, PEG-10 olive oil glycerides, PEG-13 sunflower oil glycerides, PEG-7 hydrogenated castor oil, hydrogenated palm kernel oil glyceride-PEG-6 ester, PEG-20 corn oil glycerides, PEG-18 glyceryl oleate/cocoate, PEG-40 hydrogenated castor oil, PEG-40 castor oil, PEG-60 hydrogenated castor oil, PEG-60 corn oil glycerides, PEG-54 hydrogenated castor oil, PEG-45 palm kernel oil glycerides, PEG-35 castor oil, PEG-80 glyceryl cocoate, PEG-60 almond oil glycerides, PEG-60 "evening primrose" glycerides, PEG-200 hydrogenated glyceryl palmate, PEG-90 glyceryl isostearate.

Preferred ethoxylated oils are PEG-7 glyceryl cocoate, PEG-9 coconut glycerides, PEG-40 hydrogenated castor oil, PEG-200 hydrogenated glyceryl palmate, PEG-90 glyceryl isostearate.

Preferred according to the invention are such detersive cosmetic or dermatological preparations containing preferably 0.1-20% by weight, particularly preferred 1-4% by weight of one or more ethyoxylated mono-, di-, and triglycerides of oleic acids having an average degree of ethoxylation of 3-20, preferred 5-10 ethylene oxide units.

It is advantageous to use additional anionic, nonionic, amphoteric, and/or zwifterionic surfactants in the preparations according to the present invention.

Anionic surfactants usually have carboxylate, sulfate or sulfonate groups as functional groups. In aqueous solution, they form negatively charged organic ions in acidic or neutral media. Cationic surfactants are almost exclusively characterized by the presence of a quaternary ammonium group. In aqueous solution, they form positively charged organic ions in acidic or neutral media. Amphoteric surfactants contain anionic as well as cationic groups and behave accordingly in aqueous solution, like anionic or cationic surfactants, depending on pH value. In strongly acidic media, they have a positive charge and in alkaline media, a negative charge. On the other hand, they are zwitterionic in the neutral pH range, as the following example is to illustrate:

$RNH_2^+CH_2CH_2COOHX^-$ (at pH=2) $X^-$=any anion, for example, $Cl^-$ $RNH_2^+CH_2CH_2COO^-$ (at pH=7)

$RNHCH_2CH_2COO^-B^+$ (at pH=12) $B^+$=any cation, for example $Na^+$

Typical for nonionic surfactants are polyether chains. Nonionic surfactants do not form ions in an aqueous medium.

A. Anionic Surfactants

Anionic surfactants to be used advantageously according to the invention are acylamino acids (and their salts), such as 1. Acyl glutamates, for example, sodium acyl glutamate, di-TEA-palmitoyl aspartate, and sodium caprylic/capric glutamate,
2. Acyl peptides, for example, palmitoyl-hydrolyzed milk protein, sodium cocoyl-hydrolyzed soy protein, and sodium/potassium cocoyl-hydrolyzed collagen,
3. Sarcosinates, for example, myristoyl sarcosine, TEA-lauroyl sarcosinate, sodium lauryl sarcosinate, and sodium cocoyl sarcosinate,
4. Taurates, for example, sodium lauroyl taurate and sodium methyl cocoyl taurate,
5. Acyl lactylates, lauroyl lactylate, caproyl lactylate
6. Alaninates.

Carboxylic acids and derivatives, such as
1. Carboxylic acids, for example, lauric acid, aluminum stearate, magnesium alkanolate, and zinc undecylenate,
2. Ester carboxylic acids, for example, calcium stearoyl lactylate, laureth-6 citrate, and sodium PEG-4 lauramide carboxylate.
3. Ether carboxylic acids, for example, sodium laureth-13 carboxylate and sodium PEG-6 cocamide carboxylate.

Phosphoric acid esters and salts, such as, for example, DEA oleth-10 phosphate and dilaureth-4 phosphate.

Sulfonic acids and salts, such as
1. Acyl isethionates, for example, sodium/ammonium cocoyl isethionate,
2. Alkyl aryl sulfonates,
3. Alkyl sulfonates, for example, sodium cocomonoglyceride sulfate, sodium $C_{12-14}$ olefin sulfonate, sodium lauryl sulfoacetate, and magnesium PEG-3 cocamidosulfate,
4. Sulfosuccinates, for example, dioctyl sodium sulfosuccinate, disodium laureth sulfosuccinate, disodium lauryl sulfosuccinate, and disodium undecylene amido-MEA sulfosuccinate.

and
Sulfuric acid esters, such as
1. Alkyl ether sulfate, for example, sodium, ammonium, magnesium, MIPA, TIPA laureth sulfate, sodium myrethsulfate, and sodium $C_{12-13}$ pareth sulfate, 2. Alkyl sulfates, such as, sodium, ammonium and TEA lauryl sulfate.

B. Amphoteric Surfactants

Amphoteric surfactants which may be used advantageously according to the invention are 1. Acyl/dialkyl ethylene diamine, for example, sodium acyl amphoacetate, sodium acyl amphodipropionate, disodium alkyl amphodiacetate, sodium acyl amphohydroxypropyl sulfonate, disodium acyl amphodiacetate, and sodium acyl amphopropionate,
2. N-alkylamino acids, for example, amino propyl alkyl glutamide, alkylamino propionic acid, sodium alkyl imido dipropionate, and lauroampho carboxyglycinate.

C. Nonionic Surfactants

Nonionic surfactants which can be used advantageously according to the invention are 1. Alcohols,
2. Alkanol amides, such as cocoamides MEA/DEA/MIPA,
3. Amine oxides, such as cocoamido propylamine oxide,
4. Esters that are formed by esterification of carboxylic acids with ethylene oxide, glycerin, sorbitan, or other alcohols,
5. Ethers, for example, ethoxylated/propoxylated alcohols, ethoxylated/propoxylated esters, ethoxylated/propoxylated glycerin esters, ethoxylated/propoxylated cholesterines, ethoxylated/propoxylated triglyceride esters, ethoxylated/propoxylated lanolin, ethoxylated/propoxylated polysiloxanes, propoxylated POE ethers, and alkyl polyglycosides, such as lauryl glucoside, decyl glycoside, cocoglycoside,
6. Sucrose esters, ethers,
7. Polyglycerin esters, diglycerin esters, monoglycerin esters,
8. Methyl glucose esters, esters of hydroxy acids.

The total quantity of surfactants in the finished cosmetic or dermatological preparations is selected advantageously from the range of 10-20% by weight, preferably 11-18% by weight, particularly preferred 12-16% by weight, relative to the total weight of the preparations.

Lauryl ether sulfate, alkyl amidopropyl betaine, and/or alkyl polyglucosides are selected advantageously as preferred additional surfactants.

It is advantageous in the invention to add to the preparations the least possible, a maximum 0.5%, and at best no cationic surfactants.

The detersive preparations according to the present invention are characterized as a rule by a water content of 95-5% by weight, relative to the total weight of the preparations, and are gels.

According to the invention, practically all conventional solids insoluble or sparingly soluble in aqueous systems can be selected. Preferred in the sense of the present invention are, for example, polymer particles or silicate particles having abrasive action (scrubs), particles having encapsulated active ingredients or oils, and the like (encapsulating materials: wax, polymers, natural polymers, colored particles without active ingredients, pearly luster or opacifying agents, pigments, powder raw materials, such as talcum, plant fibers, and others.

The preparations are designed advantageously so that they have a yield point of 0.5-20 Pa, preferably 1-6 Pa.

The critical shear stress of the flow curve is considered as the yield point. It can be determined according to the present invention as follows:

The flow curve is measured on a shear stress-controlled rheometer at 25° C.±1° C. with 25 mm plate/plate geometry at a gap between 0.8 mm and 1.2 mm, which is filled carefully to preserve structure. A suitable constant shear stress time ramp is prescribed, and before the test, a corresponding structure recovery time is observed, and the critical shear stress is given in the maximum of the flow curve.

The preparations are designed advantageously so that they have a tan $\delta$ of 0.05-0.6, preferably 0.1-0.5.

According to the invention, tan $\delta$ is understood as the quotient of the loss module and the memory module. tan $\delta$ is determined as follows:

Loss module and memory module are measured by a dynamic frequency test on a shear stress-controlled rheometer at 40° C.±1° C. with 25 mm plate/plate geometry at a gap between 0.8 mm and 1.2 mm, which is filled carefully to preserve structure. According to the prior art, the frequency test is conducted with a corresponding structure recovery time, and the tan $\delta$ is given in the frequency range between 0.05 rad/s and 3.0 rad/s, preferably between 0.08 rad/s and 1.0 rad/s.

The yield point can be raised by increasing the gel-former concentration.

The cosmetic and dermatological preparations according to the present invention may contain cosmetic auxiliary materials, as are conventionally used in such preparations, for example, preservatives, bactericides, perfumes, substances to prevent foaming, dyes, pigments that have a coloring effect, thickening agents, moisturizers and humectants, fats, oils, waxes or other conventional components of a cosmetic or dermatological formulation, such as alcohols, polyols, polymers, foam stabilizers, electrolytes, organic solvents, or silicone derivatives.

The preparations according to the present invention are advantageously buffered to a pH range >5.5, particularly preferred >6.0, particularly preferred 6.3-6.9.

An additional content of antioxidants is generally preferred. According to the invention, all antioxidants suited or commonly used for cosmetic and/or dermatological applications can be used as favorable antioxidants.

The antioxidants are advantageously selected from the group consisting of amino acids (for example, glycine, histidine, tyrosine, tryptophan) and their derivatives, imidazoles (for example, urocaninic acid) and their derivatives, peptides, such as D,L-carnosine, D-carnosine, L-carnosine, and their derivatives (for example, anserine), carotinoids, carotenes (for example, $\alpha$-carotene, $\beta$-carotene, $\psi$-lycopene) and their derivatives, chlorogenic acid and its derivatives, lipoic acid and its derivatives (for example, dihydrolipoic acid), aurothioglucose, propyl thiouracil and other thiols (for example, thioredoxin, glutathione, cysteine, cystine, cystamine, and their glycosyl, N-acetyl, methyl, ethyl, propyl, amyl, butyl and lauryl, palmitoyl, oleyl, γ-linoleyl, cholesteryl, and glyceryl esters), and their salts, dilauryl thiodipropionate, distearyl thiodipropionate, thiodipropionic acid and its derivatives (esters, ethers, peptides, lipids, nucleotides, nucleosides, and salts) and sulfoximine compounds (for example, buthionine sulfoximine, homocysteine sulfoximine, buthionine sulfone, penta-, hexa-, heptathionine sulfoximine) in very low compatible dosages (for example, pmole to µmole/kg), further, (metal) chelate formers (for example, α-hydroxy fatty acids, palmitic acid, phytic acid, lactoferrin), α-hydroxyacids (for example, citric acid, lactic acid, malic acid), humic acid, bile acid, bile extracts, bilirubin, biliverdin, EDTA, EGTA, and their derivatives, unsaturated fatty acids and their derivatives (for example, γ-linolenic acid, linoleic acid, oleic acid), folic acid and its derivatives, furfurylidene sorbitol and its derivatives, ubiquinone and ubiquinol and their derivatives, vitamin C and derivatives (e.g., ascorbyl palmitate, Mg-ascorbyl phosphate, ascorbyl acetate), tocopherols and derivatives (for example, vitamin E acetate), vitamin A and derivatives (vitamin A palmitate), and coniferyl benzoate of benzoin resin, rutinic acid and its derivatives, α-glycosyl rutin, ferulic acid, furfurylidene glucitol, carnosine, butylated hydroxytoluene, butylated hydroxyanisole, nordihydroguajak resin acid, nordihyrdoguajaretic acid, trihydroxy butyrophenone, uric acid and its derivatives, mannose and its derivatives, zinc and its derivatives (for example, ZnO, $ZnSO_4$), selenium and its derivatives (for example, selenium methionine), stilbene and its derivatives (for example, stilbene oxide, trans-stilbene oxide) and derivatives suitable according to the invention (salts, esters, ethers, sugars, nucleotides, nucleosides, peptides and lipids) of these named ingredients.

The quantity of the aforesaid antioxidants (one or more compounds) in the preparations is preferably from 0.001 to 30% by weight, particularly preferred 0.05-20% by weight, in particular 1-10% by weight, relative to the total weight of the preparation.

If vitamin E and/or its derivatives is/are the antioxidant(s), it is advantageous to select their concentrations in each case from the range of from 0.001 to 10% by weight, relative to the total weight of the formulation.

If vitamin A or vitamin A derivatives or carnotenes or their derivatives are the antioxidant(s), it is advantageous to select their concentrations in each case from the range of from 0.001 to 10% by weight, relative to the total weight of the formulation.

The cosmetic and/or dermatological preparations according to the present invention are prepared in ways usual for one of skill in the art, mostly in such a manner that the surface-active glucose derivatives used according to the invention are suspended with steady stirring and optionally with heating and optionally homogenized, optionally combined with other lipid components and optionally with one or more other emulsifiers, afterwards the oil phase is mixed with the aqueous phase, in which a thickening agent has been optionally incorporated, and which preferably has about the same temperature as the oil phase optionally homogenized and allowed to cool to room temperature. After cooling to room temperature, homogenization can be repeated, particularly if volatile components are still to be incorporated.

The preparations according to the present invention are particularly advantageously characterized in that gaseous, solid, and/or liquid objects are incorporated in the gels. One of skill in the art knows how the incorporation of such objects into the preparation occurs.

The following examples are to illustrate the present invention without limiting it. All quantity data, parts and percentages refer, unless otherwise stated, to the weight and the total quantity or to the total weight of the preparations.

Example Recipes

|  | Example No. | | | | | | |
| --- | --- | --- | --- | --- | --- | --- | --- |
|  | 1 | 2 | 3 | 4 | 5 | 6 | 7 |
| Sodium laureth sulfate | 13.8 | 11.0 | 9.5 | 8.5 | 12.0 | 10 | 11 |
| Cocoamidopropyl betaine | 2.65 | 3.3 | 3.8 | 1.0 | 2.1 | 4.0 | 3.3 |
| Sodium cocoyl glutamate | 1.25 | 0.75 | — | 0.5 | 0.75 | 2.0 | — |
| Aqua SF-1 | 3.00 | 2.80 | 1.50 | 2.00 | 2.20 | 2.40 | 1.80 |
| PEG-7 Glyceryl cocoate | 1.00 | 1.5 | 0.30 | — | — | — | 0.50 |
| PEG-8 Caprylic acid/capric acid triglycerides | — | — | — | 1.00 | — | 0.50 | — |
| PEG-9 Coconut oil acid glycerides | — | — | — | — | 1.50 | 0.50 | 2.50 |
| PEG-40 Hydrogenated castor oil | — | — | 0.20 | 0.50 | — | 0.50 | — |
| PEG-200 Hydrogenated glyceryl palmate | — | 0.75 | — | 0.5 | — | — | — |
| Glycol distearate | 1.0 | — | — | — | — | — | — |
| Styrene/acrylate copolymer | — | 0.5 | — | — | — | — | — |
| DMDM Hydantoin | 0.30 | 0.30 | 0.30 | 0.30 | — | 0.30 | 0.30 |
| Methyl paraben | — | — | — | — | 0.40 | — | — |
| Propyl paraben | — | — | — | — | 0.20 | — | — |
| Phenoxyethanol | — | — | — | — | 0.60 | — | — |
| Cosmospheres ® | — | 0.2 | — | — | — | 0.2 | — |
| Citric acid | q.s. | q.s. | q.s. | q.s. | q.s. | q.s. | q.s. |
| NaOH | q.s: | q.s. | q.s. | q.s. | q.s. | q.s. | q.s. |
| Perfume | 1.00 | 1.10 | 1.00 | 1.00 | 1.20 | 1.00 | 1.00 |
| Water | to 100 | to 100 | to 100 | to 100 | to 100 | to 100 | to 100 |

Aqua SF-1 is diluted with one part of the water phase and is added with stirring to the surfactant phase. Subsequently, the other recipe components except for NaOH and the suspended solid particles are added with stirring. Following pH adjustment, the suspended solid particles are stirred into the finished gel base with the least possible shear.

|  | Example No. | | | | |
|---|---|---|---|---|---|
|  | 8 | 9 | 10 | 11 | 12 |
| Sodium laureth sulfate | 13.2 | 11.5 | 10 | 9.2 | 8.5 |
| Cocoamidopropyl betaine | 2.0 | 0.75 | 2.5 | 3.0 | 1.25 |
| Decyl glucoside | 1.25 | 1.50 | 2.0 | 0.8 | 0.75 |
| Aqua SF-1 | 1.50 | 1.80 | 2.00 | 2.5 | 3.0 |
| PEG-7 Glyceryl cocoate | — | — | — | 0.50 | 1.00 |
| PEG-6 Caprylic acid/capric acid triglycerides | — | — | 1.0 | — | — |
| PEG-9 Coconut fatty acid glycerides | 1.00 | 3.00 | — | 0.50 | — |
| PEG-40 Hydrogenated castor oil | 0.50 | — | 0.50 | 0.50 | — |
| PEG-200 Hydrogenated glyceryl palmate | — | — | 0.5 | — | 0.5 |
| Glycol distearate |  |  | 1.0 |  |  |
| Styrene/acrylate copolymer |  |  |  | 0.5 |  |
| DMDM Hydantoin | 0.30 | 0.30 | 0.30 | 0.30 | 0.30 |
| Unispheres ® | 0.25 | 0.1 | 0.20 |  |  |
| Timiron Artic Silver |  |  |  |  | 0.05 |
| Citric acid | q.s. | q.s. | q.s. | q.s. | q.s. |
| NaOH | q.s | q.s. | q.s. | q.s. | q.s. |
| Perfume | 1.30 | 1.00 | 1.00 | 1.10 | 1.20 |
| Water | to 100 | to 100 | to 100 | to 100 | to 100 |

Aqua SF-1 is diluted with one part of the water phase and is added with stirring to the surfactant phase. Subsequently, the other recipe components except for NaOH and the suspended solid particles are added with stirring. Following pH adjustment, the suspended solid particles are stirred into the finished gel base with the least possible shear.

|  | Example No. | | | | | |
|---|---|---|---|---|---|---|
|  | 13 | 14 | 15 | 16 | 17 | 18 |
| Sodium myreth sulfate | 5 | 4 | 6 | 4 | 2.5 | 5 |
| Decyl glucoside | 2.5 | — | — | 3 | 0.7 | 2.5 |
| Sodium cocoampho acetate | 6.5 | 7 | 8 | 3 | — | 6.5 |
| Cocamidopropyl betalne | — | — | — | — | 3.3 | — |
| Aqua SF-1 | 2.0 | 2.8 | 2.2 | 3.0 | 2.4 | 2.0 |
| PEG-7 Glyceryl cocoate | 0.5 | 0.5 | — | — | 0.5 |  |
| PEG-6 Caprylic acid/capric acid triglycerides | — | — | 1.0 | — | 0.5 | 0.75 |
| PEG-9 Coconut fatty acid glycerides | — | — | — | 0.5 | — | — |
| PEG-200 Hydrogenated glyceryl palmitate | 0.4 | 0.4 | 0.4 | — | — | 0.4 |
| PEG-40 Hydrogenated castor oil | 1.0 | — | — | 0.5 | — | 1.0 |
| Glycol distearate | — | 1 | — | — | — | — |
| Styrene/acrylate copolymer | — | — | — | 0.5 | — | — |
| Diammonium citrate | 0.12 | 0.12 | 0.12 | 0.12 | 0.12 | 0.12 |
| DMDM Hydantoin | 0.3 | 0.3 | 0.3 | 0.3 | — | 0.3 |
| Methyl paraben | — | — | — | — | 0.4 | — |
| Propyl paraben | — | — | — | — | 0.2 | — |
| Phenoxy ethanol | — | — | — | — | 0.6 | — |
| Polyethylene beads | 2.0 |  |  |  | 2.0 |  |
| Cosmospheres ® |  |  | 0.2 | 0.22 |  | 0.2 |
| Citric acid | q.s. | q.s. | q.s. | q.s. | q.s. | q.s. |
| NaOH | q.s. | q.s. | q.s. | q.s. | q.s. | q.s. |
| Perfume | 1.00 | 1.00 | 1.30 | 1.00 | 1.20 | 1.20 |
| Water | to 100 | to 100 | to 100 | to 100 | to 100 | to 100 |

Aqua SF-1 is diluted with one part of the water phase and is added with stirring to the surfactant phase. Subsequently, the other recipe components except for NaOH and the suspended solid particles are added with stirring. Following pH adjustment, the suspended solid particles are stirred into the finished gel base with the least possible shear.

|  | Example No. | | | | | | | | |
|---|---|---|---|---|---|---|---|---|---|
|  | 19 | 20 | 21 | 22 | 23 | 24 | 25 | 26 | 27 |
| Sodium laureth sulfate | 13.0 | 11.0 | 9.0 | 8.5 | 12.0 | 10 | 11 | — | 10 |
| Cocoamido propylbetaine | 0.50 | 1.5 | 2.0 | 1.0 | | 4.0 | 2.5 | 4.0 | 4.0 |
| Decyl glucoside | — | — | — | — | 1.10 | — | — | 4.0 | |
| Sodium cocoyl glutamate | 1.50 | 0.5 | 1.0 | 0.5 | 0.75 | 2.0 | 3.0 | 1.5 | 2.0 |
| Aqua SF-1 | 3.00 | 1.50 | 1.75 | 2.00 | 2.20 | 2.40 | 3.5 | 2.8 | 2.4 |
| Polyquaternium-10 | | | | 0.20 | | | | | |
| PEG-6 Caprylic acid/capric acid triglycerides | | 0.75 | 1.0 | | | 1.0 | | | |
| PEG-40 Hydrogenated castor oil | 1.0 | 1.0 | 1.0 | 1.0 | 1.0 | 1.0 | 1.0 | 1.2 | |
| Glycol distearate | 1.0 | — | — | — | — | — | — | | |
| Styrene/acrylate copolymer | | 0.5 | — | — | — | — | — | | 0.5 |
| DMDM Hydantoin | 0.30 | 0.30 | 0.30 | 0.30 | | 0.30 | 0.30 | 0.30 | |
| Methyl paraben | — | — | — | — | 0.40 | — | — | | 0.40 |
| Propyl paraben | — | — | — | — | 0.20 | — | — | | 0.20 |
| Phenoxy ethanol | — | — | — | — | 0.60 | — | — | | 0.60 |
| Cosmospheres ® | | 0.25 | | | | | | | |
| Unispheres ® | 0.3 | | | | | 0.20 | | | |
| Titanium dioxide | | | | | | | | | 0.3 |
| Timiron Artic Silver | | | | | | | | 0.05 | |
| Polyethylene beads | | | | | | | | | 0.2 |
| Dye | | 0.05 | | | | | | | |
| Citric acid | q.s. | q.s. | q.s. | q.s. | q.s. | q.s. | q.s. | q.s. | q.s. |
| NaOH | q.s. | q.s. | q.s. | q.s. | q.s. | q.s. | q.s. | q.s. | q.s. |
| Perfume | 1.00 | 1.00 | 1.50 | 0.90 | 1.00 | 1.00 | 0.80 | 1.00 | 1.20 |
| Water | to 100 | to 100 | to 100 | to 100 | to 100 | to 100 | to 100 | to 100 | ad 100 |

Aqua SF-1 is diluted with one part of the water phase and is added with stirring to the surfactant phase. Subsequently, the other recipe components except for NaOH and the suspended solid particles are added with stirring. Following pH adjustment, the suspended solid particles are stirred into the finished gel base with the least possible shear.

What is claimed is:

1. A cosmetic or dermatological cleansing preparation, wherein the preparation comprises
   (a) one or more surfactants selected from disodium lauroyl glutamate, disodium cocoyl glutamate, disodium myristoyl glutamate, disodium stearoyl glutamate, and disodium tallowyl glutamate,
   (b) optionally, one or more further surfactants,
   (c) one or more gel-forming acrylate thickeners selected from cross-linked, alkali-swellable acrylate copolymers,
   (d) up to 20% by weight, based on a total weight of the preparation, of ethoxylated mono-, di-, and triglycerides of carboxylic acids having from 8 to 22 carbon atoms, and
   (e) optionally, suspended objects selected from one or more of solid particles, gas bubbles and liquid droplets;
   a total concentration of (a) plus (b) being from 10% to 20% by weight, relative to a total weight of the preparation.

2. The preparation of claim 1, wherein (a) is present in a concentration of from 0.1% to 5% by weight, relative to a total weight of the preparation.

3. The preparation of claim 1, wherein (a) is present in a concentration of from 0.5% to 4% by weight.

4. The preparation of claim 1, wherein (c) comprises a copolymer of (i) one or more monomers selected from acrylic acid, methacrylic acid, itaconic acid, fumaric acid, crotonic acid, aconitic acid, and maleic acid, (ii) one or more further α,β-ethylenically unsaturated monomers and (iii) one or more polyunsaturated monomers suitable for partial cross-linking.

5. The preparation of claim 1, wherein (c) comprises a copolymer of (i) one or more monomers selected from acrylic acid, methacrylic acid, itaconic acid, fumaric acid, crotonic acid, aconitic acid, and maleic acid, (ii) one or more further α,β-ethylenically unsaturated monomers selected from compounds of (a) general formula $CH_2=CXY$ with $X=H$, Cl, $C_1$-$C_{30}$ alkyl, $CH_2$—$(C=O)O(CH_2$—$CH_2$—$O)_x$—$R^3$, $CH_2$—$C(=O)NH(CH_2$—$CH_2$—$O)_x$—$R^3$, or $CH_2$—$CH_2=(CH_2$—$CH_2$—$O)_x$—$R^3$ with $x=1$-$100$ and $R^3=C_1$-$C_{30}$ alkyl, and $Y=COOR$, $C_6H_4R$, CN, $CONH_2$, Cl, $NC_4H_6O$, $NH(CH_2)_3COOH$, $NHCOCH_3$, $CONHC(CH_3)_3$, $CON(CH_3)_2$, $CH=CH_2$, $C_1$-$C_{18}$ alkyl, hydroxy-$C_1$-$C_{18}$ alkyl, $C(=O)O(CH_2$—$CH_2$—$O)_x$—$R^3$, $C(=O)NH(CH_2$—$CH_2$—$O)_x$—$R^3$, $CH_2$—$(CH_2$—$CH_2$—$O)_x$—$R^3$ with $x=1$-$100$ and $R^3=C_1$-$C_{30}$ alkyl, or (b) general formula $CH_2=CH(OCOR^2)$ with $R^2=C_1$-$C_{18}$ alkyl, or (c) formula $CH_2=CH_2$ or formula $CH_2=CHCH_3$, and (iii) one or more polyunsaturated monomers suitable for partial cross-linking.

6. The preparation of claim 1, wherein (c) is present in a concentration of from 0.3% to 6% by weight, relative to a total weight of the preparation.

7. The preparation of claim 5, wherein (c) is present in a concentration of from 0.5% to 4% by weight, relative to a total weight of the preparation.

8. The preparation of claim 1, wherein (d) comprises one or more ethoxylated glycerin fatty acids.

9. The preparation of claim 8, wherein the one or more ethoxylated glycerin fatty acids are selected from PEG-10 olive oil glycerides, PEG-11 avocado oil glycerides, PEG-11 cocoa butter glycerides, PEG-13 sunflower oil glycerides, PEG-15 glyceryl isostearate, PEG-9 coconut fatty acid glycerides, PEG-54 hydrogenated castor oil, PEG-7 hydrogenated castor oil, PEG-60 hydrogenated castor oil, jojoba oil ethoxylate, PEG-26 jojoba fatty acids, PEG-26 jojoba alcohol, glycereth-5 cocoate, PEG-9 coconut fatty acid glycerides, PEG-7 glyceryl cocoate, PEG-45 palm kernel oil glycerides, PEG-35 castor oil, olive oil PEG-7 ester, PEG-6 caprylic acid/capric acid triglycerides, PEG-10 olive oil glycerides, PEG-13 sunflower oil glycerides, PEG-7 hydrogenated castor oil, hydrogenated palm kernel oil glyceride-PEG-6 ester, PEG-20 corn oil glycerides, PEG-18 glyceryl oleate/cocoate, PEG-40 hydrogenated castor oil, PEG-40 castor oil, PEG-60 hydrogenated castor oil, PEG-60 corn oil glycerides, PEG-54 hydrogenated castor oil, PEG-45 palm kernel oil glycerides, PEG-35 castor oil, PEG-80 glyceryl cocoate, PEG-60 almond oil glycerides, PEG-60 evening primrose glycerides, PEG-200 hydrogenated glyceryl palmate, and PEG-90 glyceryl isostearate.

10. The preparation of claim 1, wherein the preparation comprises from 0.1% to 20% by weight of one or more ethyoxylated mono-, di-, and triglycerides of oleic acids having an average degree of ethoxylation of from 3 to 20 ethylene oxide units.

11. The preparation of claim 1, wherein the preparation comprises from 1% to 4% by weight of (d).

12. The preparation of claim 11, wherein the preparation comprises at least 12% by weight of (a) plus (b).

13. The preparation of claim 1, wherein the preparation comprises not more than 0.5% by weight of cationic polymers.

14. The preparation of claim 1, wherein the preparation is free of cationic polymers.

15. A cosmetic or dermatological cleansing preparation, wherein the preparation comprises
  (a) at least one surfactant selected from disodium acyl glutamates,
  (b) one or more further surfactants,
  (c) one or more gel-forming thickeners selected from cross-linked, alkali-swellable acrylate copolymers comprising a copolymer of (i) one or more monomers selected from acrylic acid, methacrylic acid, itaconic acid, fumaric acid, crotonic acid, aconitic acid, and maleic acid, (ii) one or more further α,β-ethylenically unsaturated monomers and (iii) one or more polyunsaturated monomers suitable for partial cross-linking,
  (d) up to 20% by weight, based on a total weight of the preparation, of ethoxylated mono, di-, and triglycerides of carboxylic acids having from 8 to 22 carbon atoms,
  (e) from 0.1% to 20% by weight of one or more ethyoxylated mono-, di-, and triglycerides of oleic acids having an average degree of ethoxylation of from 3 to 20 ethylene oxide units,
  (f) optionally, suspended objects selected from one or more of solid particles, gas bubbles and liquid droplets;
  a total concentration of (a) plus (b) being from 10% to 20% by weight, relative to a total weight of the preparation.

16. The preparation of claim 15, wherein (b) comprises one or more surfactants selected from lauryl ether sulfates, alkyl amidopropylbetaines and alkyl polyglucosides.

17. The preparation of claim 16, wherein (c) is present in a concentration of from 0.5% to 4% by weight, relative to a total weight of the preparation.

18. The preparation of claim 16, wherein the preparation is free of cationic polymers.

19. The preparation of claim 16, wherein (a) comprises from 0.5% to 5% by weight of one or more of disodium lauroyl glutamate, disodium cocoyl glutamate, disodium myristoyl glutamate, disodium stearoyl glutamate, and disodium tallowyl glutamate.

20. The preparation of claim 16, wherein the preparation comprises at least 12% by weight of (a) plus (b).

21. The preparation of claim 15, wherein the preparation has a transmission value of >70%.

22. The preparation of claim 15, wherein the preparation has at least one of a yield point of from 1 to 6 Pa and a tan δ of from 0.1 to 0.5.

23. The preparation of claim 15, wherein the preparation has a pH of from 6.3 to 6.9.

24. A cosmetic or dermatological cleansing preparation, wherein the preparation comprises
  (a) one or more surfactants selected from disodium lauroyl glutamate, disodium cocoyl glutamate, disodium myristoyl glutamate, disodium stearoyl glutamate, and disodium tallowyl glutamate,
  (b) one or more surfactants selected from lauryl ether sulfates, alkyl amidopropylbetaines and alkyl polyglucosides,
  (c) one or more gel-forming thickeners selected from cross-linked, alkali-swellable copolymers of monomers comprising (i) one or more monomers selected from acrylic acid, methacrylic acid, itaconic acid, fumaric acid, crotonic acid, aconitic acid, and maleic acid, (ii) one or more further α,β-ethylenically unsaturated monomers selected from compounds of (a) general formula $CH_2$=CXY with X=H, Cl, $C_1$-$C_{30}$ alkyl, $CH_2$—(C(=O)O($CH_2$—$CH_2$—O)$_x$—$R^3$, $CH_2$—C(=O)NH($CH_2$—$CH_2$—O)$_x$—$R^3$, or $CH_2$—$CH_2$=($CH_2$—$CH_2$—O)$_x$—$R^3$ with x=1-100 and $R^3$=$C_1$-$C_{30}$ alkyl, and Y=COOR, $C_6H_4R$, CN, $CONH_2$, Cl, $NC_4H_6O$, $NH(CH_2)_3COOH$, $NHCOCH_3$, $CONHC(CH_3)_3$, $CON(CH_3)_2$, CH=$CH_2$, $C_1$-$C_{18}$ alkyl, hydroxy-$C_1$-$C_{18}$ alkyl, C(=O)O($CH_2$—$CH_2$—O)$_x$—$R^3$, C(=O)NH($CH_2$—$CH_2$—O)$_x$—$R^3$, $CH_2$—($CH_2$—$CH_2$—O)$_x$—$R^3$ with x=1-100 and $R^3$=$C_1$-$C_{30}$ alkyl, or (b) general formula $CH_2$=CH(OCO$R^2$) with $R^2$=$C_1$-$C_{18}$ alkyl, or (c) formula $CH_2$=$CH_2$ or formula $CH_2$=$CHCH_3$, and (iii) one or more polyunsaturated monomers suitable for partial cross-linking,
  (d) up to 20% by weight, based on a total weight of the preparation, of ethoxylated mono, di-, and triglycerides of carboxylic acids having from 8 to 22 carbon atoms, and
  (e) optionally, suspended objects selected from one or more of solid particles, gas bubbles and liquid droplets;
  and wherein the preparation has a yield point of from 0.5 to 20 Pa, a tan δ of from 0.05 to 0.6, and a pH of >5.5.

25. The preparation of claim 24, wherein the preparation has a transmission value of >70%.

26. The preparation of claim 25, wherein the preparation has at least one of a yield point of from 1 to 6 Pa, a tan δ of from 0.1 to 0.5, and a pH of >6.0.

27. The preparation of claim 24, wherein (a) comprises from 0.5% to 5% by weight of one or more of disodium lauroyl glutamate, disodium cocoyl glutamate, disodium myristoyl glutamate, disodium stearoyl glutamate, and disodium tallowyl glutamate.

28. The preparation of claim 27, wherein the preparation comprises from 12% to 16% % by weight of (a) plus (b).

29. The preparation of claim 24, wherein (e) is present.

30. The preparation of claim 24, wherein the preparation is free of cationic polymers.

31. The preparation of claim 24, wherein (d) comprises one or more ethoxylated glycerin fatty acids selected from PEG-10 olive oil glycerides, PEG-11 avocado oil glycerides, PEG-11 cocoa butter glycerides, PEG-13 sunflower oil glycerides, PEG-15 glyceryl isostearate, PEG-9 coconut fatty acid glycerides, PEG-54 hydrogenated castor oil, PEG-7 hydrogenated castor oil, PEG-60 hydrogenated castor oil, jojoba oil ethoxylate, PEG-26 jojoba fatty acids, PEG-26 jojoba alcohol, glycereth-5 cocoate, PEG-9 coconut fatty acid glycerides, PEG-7 glyceryl cocoate, PEG-45 palm kernel oil glycerides, PEG-35 castor oil, olive oil PEG-7 ester, PEG-6 caprylic acid/capric acid triglycerides, PEG-10 olive oil glycerides, PEG-13 sunflower oil glycerides, PEG-7 hydrogenated castor oil, hydrogenated palm kernel oil glyceride-PEG-6 ester, PEG-20 corn oil glycerides, PEG-18 glyceryl oleate/cocoate, PEG-40 hydrogenated castor oil, PEG-40 castor oil, PEG-60 hydrogenated castor oil, PEG-60 corn oil glycerides, PEG-54 hydrogenated castor oil, PEG-45 palm kernel oil glycerides, PEG-35 castor oil, PEG-80 glyceryl cocoate, PEG-60 almond oil glycerides, PEG-60 evening primrose glycerides, PEG-200 hydrogenated glyceryl palmate, and PEG-90 glyceryl isostearate.

* * * * *